United States Patent
Brodnick (10) Patent No.: US 7,277,743 B2
(45) Date of Patent: Oct. 2, 2007

(54) PATIENT MONITORING SYSTEM

(75) Inventor: Don Brodnick, Cedarburg, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 415 days.

(21) Appl. No.: 10/369,852

(22) Filed: Feb. 20, 2003

(65) Prior Publication Data

US 2004/0167384 A1    Aug. 26, 2004

(51) Int. Cl.
    *A61B 5/0408*    (2006.01)
(52) U.S. Cl. .................................. 600/382; 600/513
(58) Field of Classification Search ............ 600/509, 600/513, 393, 372, 390, 520, 382, 394, 324, 600/333; 439/909
    See application file for complete search history.

(56) References Cited

U.S. PATENT DOCUMENTS

| | | | | |
|---|---|---|---|---|
| 4,328,814 A | * | 5/1982 | Arkans | 600/393 |
| 4,690,148 A | * | 9/1987 | Hess | 600/374 |
| 4,695,955 A | * | 9/1987 | Faisandier | 600/300 |
| 4,854,323 A | | 8/1989 | Rubin | |
| 4,889,131 A | * | 12/1989 | Salem et al. | 600/484 |
| 5,327,888 A | * | 7/1994 | Imran | 600/393 |
| 5,341,806 A | * | 8/1994 | Gadsby et al. | 600/393 |
| 5,353,793 A | * | 10/1994 | Bornn | 600/386 |
| 5,546,950 A | * | 8/1996 | Schoeckert et al. | 600/508 |
| 6,115,623 A | | 9/2000 | McFee | |
| 6,494,829 B1 | * | 12/2002 | New et al. | 600/300 |
| 6,497,659 B1 | * | 12/2002 | Rafert | 600/331 |
| 6,516,289 B2 | * | 2/2003 | David | 600/384 |
| 2001/0000526 A1 | * | 4/2001 | Gopinathan et al. | 600/300 |
| 2002/0019166 A1 | | 2/2002 | Ubby et al. | |

FOREIGN PATENT DOCUMENTS

| | | |
|---|---|---|
| CN | 2245957 Y | 1/1997 |
| WO | WO 02/03395 | 1/2002 |
| WO | WO/03070097 A1 * | 8/2003 |

* cited by examiner

*Primary Examiner*—Scott M. Getzow
(74) *Attorney, Agent, or Firm*—Andrus, Sceales, Starke & Sawall, LLP (57) ABSTRACT

A patient monitoring system is disclosed. The patient monitoring system includes at least one monitoring cable, a plurality of connecting wires, and a plurality of connectors. The plurality of connecting wires are housed within an outer covering and each extend from a first end to a second end of the at least one monitoring cable. The plurality of connectors are arranged in an in-line sequence from the first end to the second end of the at least one monitoring cable and may include at least one ECG connector and at least one non-ECG connector. The patient monitoring system may also be configured to provide strain relief for the at least one cable.

26 Claims, 6 Drawing Sheets

PATIENT MONITORING SYSTEM

BACKGROUND OF THE INVENTION

The field of the invention is patient monitoring systems. More particularly, the invention relates to an improved patient monitoring cable apparatus for in-line connection of multiple sensors.

An electrocardiogram (ECG) is used to monitor the heart activity of patients. To obtain information and monitor the electrical activity of the heart, a patient is connected to an ECG monitoring system with ECG cables. One type of ECG cable for monitoring is referred to as a 12-lead ECG. A 12-lead ECG requires the use of 10 electrodes for acquiring ECG signals. Generally, each of the ten electrodes require a separate connecting wire in the ECG cable. Further, multiple cables and connectors are often required when doctors must monitor more than just ECG signals. For example, when a doctor needs to monitor the blood pressure, pulse oximetry, and/or ECG of a patient, the doctor will usually use different cables and connectors for each monitoring instrument. The large number of cables and connectors can be bulky and difficult to organize. Therefore, there exists a need for an ECG cable with fewer wires to avoid the clutter and tangling of multiple wires and/or cables. Further, there exists a need for an ECG cable with improved signal quality and reduced artifact. In addition, there exists a need for an ECG cable that has improved convenience for simultaneously obtaining ECG signals as well as non-ECG signals, from blood pressure sensors, respiration sensors, pulse oximetry sensors, ECG sensors, etc.

SUMMARY OF THE INVENTION

One embodiment of the present invention provides a monitoring cable for use with a patient monitoring system. The monitoring cable includes a first end and a second end, an outer sheathing extending from the first end to the second end, a plurality of connecting wires, and a plurality of connectors. The plurality of connecting wires are each housed within the outer sheathing. The plurality of connectors are arranged along the monitoring cable to correspond with a desired location on the patient and are each coupled to at least one connecting wire.

Another embodiment of the present invention provides a monitoring cable for use with a patient monitoring system. The monitoring cable includes a plurality of connecting wires and a plurality of sensors. The plurality of connecting wires are housed within an outer covering and extend from a first end to a second end of the monitoring cable. The plurality of sensors are arranged in an in-line sequence from the first end to the second end of the monitoring cable and are coupled to at least one connecting wire. In addition, the plurality of sensors include a right leg electrode positioned as a first sensor in the in-line sequence and at least one non-ECG sensor.

Another embodiment of the present invention provides a patient monitoring system. The patient monitoring system includes a plurality of connecting wires, an interface, a plurality of connectors, and monitoring equipment coupled to the interface located at the first end of the monitoring cable. The plurality of connecting wires are housed within an outer sheathing of at least one monitoring cable. Further, the plurality of connecting wires each extend from a first end to a second end of the at least one monitoring cable. The interface is located at the first end of the at least one monitoring cable and includes a plurality of contact portions each connected to a respective one of the plurality of connecting wires. The plurality of connectors are each coupled to at least one of the plurality of connecting wires.

Another embodiment of the present invention provides a method of providing data. The method includes the steps of acquiring data using a plurality of sensors arranged in an in-line sequence from a first end to a second end of a monitoring cable, transmitting data acquired from the plurality of sensors to a plurality of connectors coupled with the plurality of sensors, and transmitting data from the plurality of connectors through a plurality of connecting wires each coupled with at least one of the plurality of connectors. The plurality of sensors include a right leg electrode positioned as a first sensor in the in-line sequence, a left hipbone electrode positioned as a second sensor in the in-line sequence, at least one midsection electrode positioned after the second sensor in the in-line sequence, a right side superior electrode positioned after the at least one midsection electrode in the in-line sequence, and a left side superior electrode positioned after the right side superior electrode in the in-line sequence. The plurality of connecting wires are housed within an outer cable and each extend from a first end to a second end of the outer cable.

Another embodiment of the present invention provides a system for monitoring a patient including a means for receiving ECG data through ECG data sensors from a patient and a means for transferring the ECG data from the ECG data sensors to monitoring equipment. Further, the ECG data sensors include a first sensor that is positionable on the patient to provide strain relief for the system.

DESCRIPTION OF THE PREFERRED EMBODIMENT

Figures 1A, 1B:
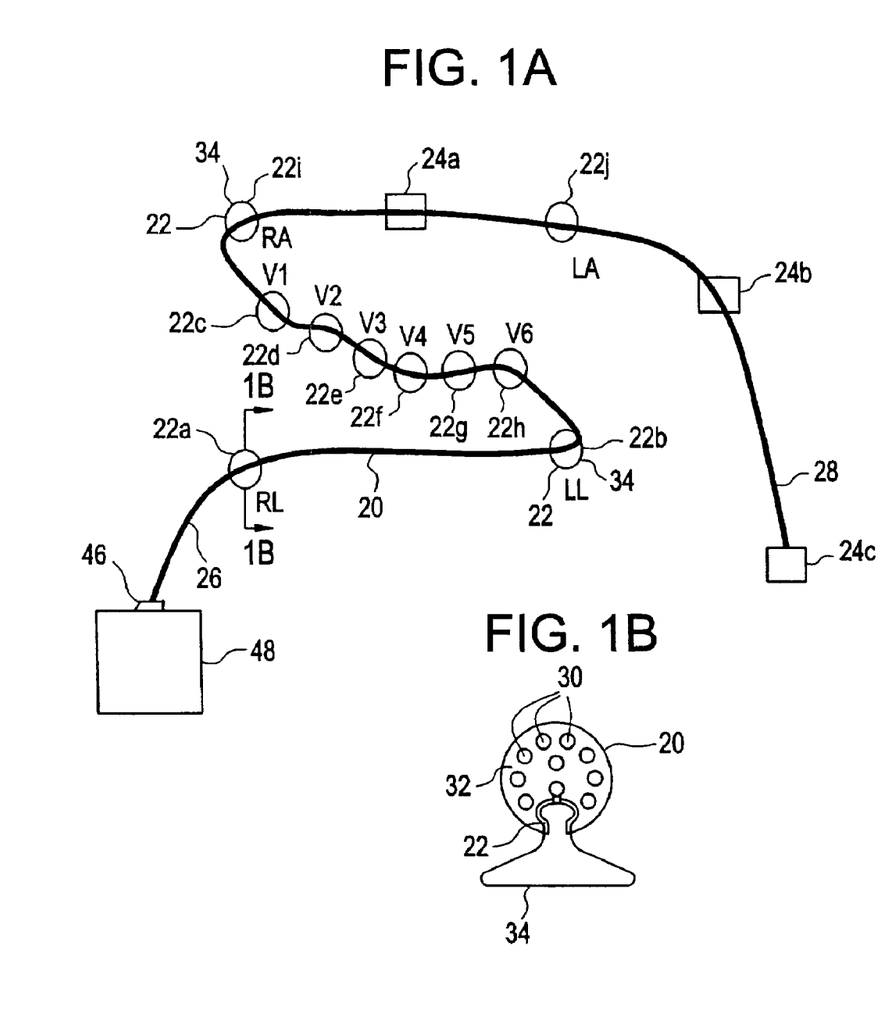
FIG. 1A is a plan view of a monitoring cable according to an exemplary embodiment.
FIG. 1B is a cross-sectional view of a monitoring cable taken along line 1B according to an exemplary embodiment.

Referring to FIGS. 1A and 1B, the major components of a patient monitoring system are shown according to an exemplary embodiment. FIG. 1A shows a monitoring cable 20 for use with a patient. Cable 20 includes a first end 26 and a second end 28. First end 26 may be coupled to an instrument 48 by way of mating connector 46. Alternatively, first end 26 may simultaneously be coupled to multiple instruments 48. As shown in FIG. 1B, cable 20 also includes connecting wires 30. Each of the connecting wires 30 are housed within an outer sheathing or covering 32 and extend from first end 26 to second end 28. This configuration allows each wire 30 to be electrically insulated from one another. Cable 20 may be substantially circular in cross-section. In other embodiments, cable 20 is substantially rectangular in cross-section. Alternatively, cable 20 may be a variety of different shapes (i.e., flat, rounded, triangular, curved, arced, etc.).

Cable 20 may include multiple connectors 22, as indicated by connectors 22a through 22j. Each of the connectors 22a through 22j are coupled to at least one of the connecting wires 30. Cable 20 may also include a housing 23 between sensor 34 and connecting wires 30 to guide sensor 34 into a position for obtaining data. Referring to FIG. 1B, connectors 22a through 22j may be coupled to sensors 34 for obtaining data from a patient. The number of connectors 22 that are coupled to sensors can vary depending on the circumstances of a particular instance. For example, all of connectors 22a through 22j may be coupled to sensors if necessary for a given patient. Alternatively, only some of connectors 22a through 22j may be coupled to sensors if fewer sensors are needed. Connectors 22a through 22j are positioned between ends 26 and 28 to correspond with desired locations for obtaining data on patients.

Figure 2:
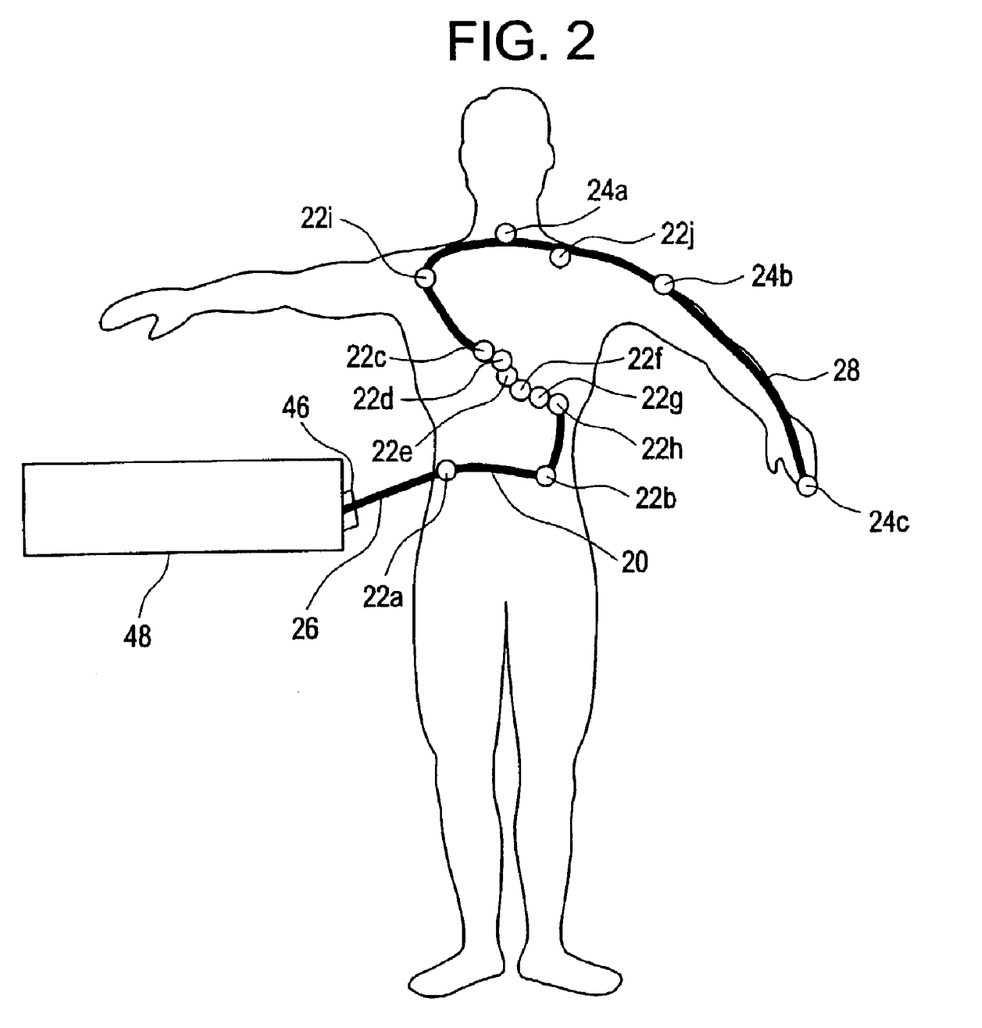
FIG. 2 shows placement of the monitoring cable of FIG. 1A on a patient according to an exemplary embodiment.

As shown in FIG. 2, connector 22a may be coupled to a sensor and positioned on the right leg of a patient to produce a right leg (RL) ECG signal. Similarly, connector 22b may be attached to a sensor and placed on the left leg of a patient to produce a left leg (LL) ECG signal. Each of connectors 22c through 22h are connected to sensors providing chest signals to the electrocardiograph. These sensors and connecting wires are sometimes designated V1 through V6 in the industry as shown in FIG. 1. The sensors are placed on the chest of a patient with sensor V1 connected to connector 22c and located near the sternum of the patient. Further, sensor V6 is connected to connector 22h and is positioned near the left armpit of the patient. Sensors V2 through V5 are connected to 22d through 22g, respectively, between sensors V1 and V6. Connector 22i is coupled with a sensor and located near the right arm of a patient to produce a right arm (RA) ECG signal. Similarly, connector 22j is coupled with a sensor and located near the left arm of a patient to produce a left arm (LA) ECG signal.

As shown in FIG. 2, connector 22a is coupled to the right leg (RL) sensor in order to provide an improved system for obtaining patient data. Specifically, the ECG is particularly insensitive to tugging on the RL sensor because the RL is not an input to any of the ECG sense amplifiers. Therefore, the RL sensor acts as a buffer to certain strain in cable 20 due to many factors including extraneous movement, tugging, bumping, or other disruption. In effect, by using the RL electrode as the first sensor, all remaining connections to sensors are less likely to become pulled or dislodged during use of cable 20. The RL electrode may be attached at any number of locations on a patient to provide the strain relief benefit. For example, the RL electrode may be placed near or on the right leg of a patient. According to a preferred embodiment of the present invention, the RL electrode is placed within about 20 inches of where the LL electrode is placed on a patient. This distance allows greater flexibility in attaching cable 20 to a patient from different angles. According to alternative embodiments, any number of sensors or connectors could be used to provide strain relief for cable 20. For example, a non-ECG sensor could be attached to a connector and positioned on a patient near the right leg and/or side of a patient.

Cable 20 may also include connectors 24, as shown by connectors 24a through 24c. Connectors 24a through 24c may be coupled to non-ECG sensors for obtaining non-ECG data. Thus, cable 20 may be used simultaneously for obtaining ECG data and non-ECG data. This eliminates the need for multiple cables or attachments during patient monitoring. For example, connector 24a may be attached to a respiration sensor for obtaining respiration data on a patient. Connector 24a may be positioned between connectors 22i and 22j, near a patient's throat or neck. Similarly, connector 24b may be attached to a non-invasive blood pressure sensor for obtaining blood pressure data on a patient. Connector 24b may be positioned after connector 22j near a patient's arm. Further, connector 24c may be attached to a pulse oxygen sensor for obtaining pulse oxygen data on a patient. Connector 24c may be positioned after connector 22j near a patient's finger, hand, ear lobe, or other suitable location.

According to alternative embodiments of the present invention, a multitude of connectors may be used to couple with any number or variety of sensors for obtaining other types of data on a patient. For example, cable 20 may be connected to a body position or activity sensor, a skin galvonic response sensor, a skin temperature sensor, etc. Further, connectors 22, 24 may be configured such that certain connectors can only be connected to certain types of sensors. For example, one connector 22 (e.g., an ECG connector) may only couple with an ECG sensor, whereas a second connector 24 (e.g., a non-ECG connector) may only couple with a non-ECG sensor. Alternatively, each connector 22 may be universally adaptable to both ECG connectors and non-ECG connectors. The possibility of numerous variations among connectors and sensors as well as the ability to attach a large number of non-ECG sensors to a patient with cable 20 helps eliminate cable clutter and thereby improve patient comfort and mobility. Furthermore, the reduced number of cables required improves care giver management by simplifying the overall connection process.

Figure 3A:
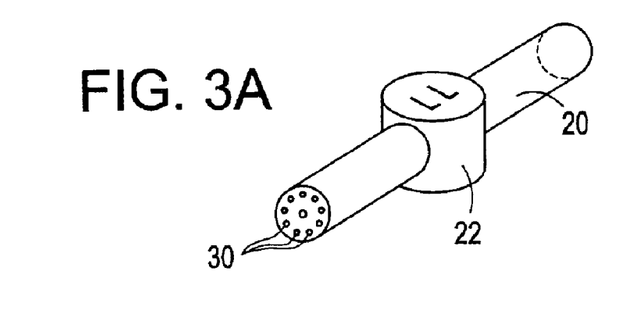
FIG. 3A is a top perspective view of a patient monitoring cable including an externally integrated connector according to an exemplary embodiment.
Figure 3B:
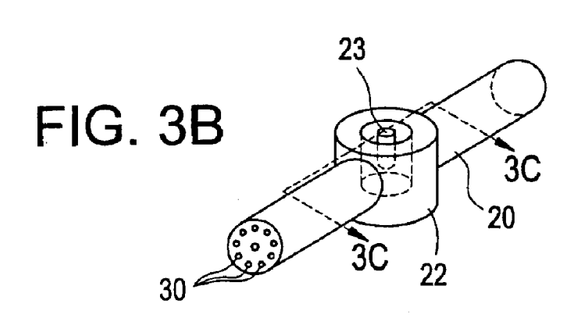
FIG. 3B is a bottom perspective view of a patient monitoring cable including an externally integrated connector according to an exemplary embodiment.
Figure 3C:
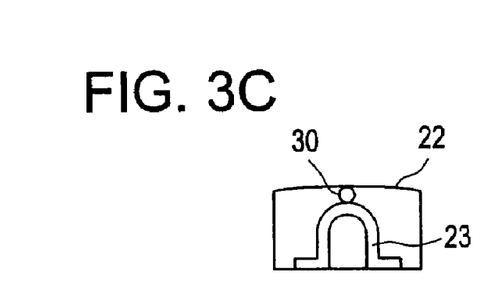
FIG. 3C is a cross-sectional view of the externally integrated connector taken along line 3C according to an exemplary embodiment.
Figure 3D:
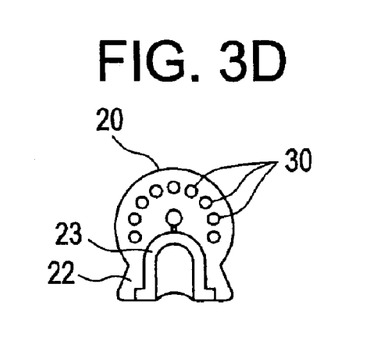
FIG. 3D is a cross-sectional view of a patient monitoring cable including an internally integrated connector according to an exemplary embodiment.
Figure 3E:
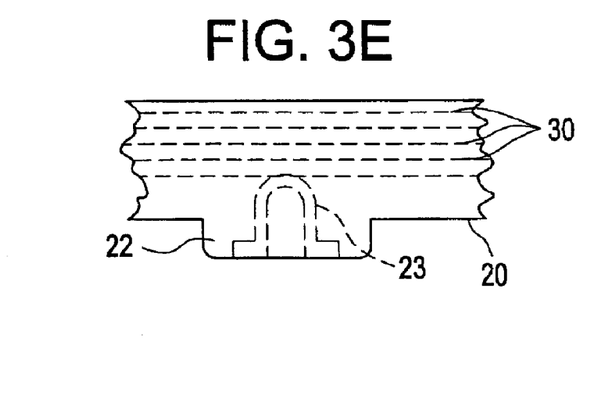
FIG. 3E is a side view of a patient monitoring cable including an internally integrated connector according to an exemplary embodiment.

Referring to FIGS. 3A-3E, each of the connectors 22a through 22j and 24a through 24c may be internally integrated within cable 20 or they may be externally integrated as part of monitoring cable 20. FIGS. 3A-3C provide one example of how a connector may have an externally integrated configuration with cable 20. For example, FIG. 3A shows a perspective view of externally integrated connector 22 as it would be seen from above cable 20. Connector 22 has a generally obtuse (e.g., rounded, smooth, etc.) shape to minimize any interference with other connectors or parts of cable 20. This configuration maximizes the total number of smoothed edges. FIG. 3B shows a perspective view of externally integrated connector 22 as it would be seen from below cable 20. Connector 22 includes housing 23 that can guide a connector into place for transmitting data. Housing 23 may be made from any suitable material (e.g., conductive metal) for allowing data to be transferred from the patient to instrument 48. The externally integrated connector 22 shown in FIGS. 3A, 3B is merely exemplary. In other words, externally integrated connector 22 may have any number of different shapes, configurations, forms, etc. FIG. 3C is a side cross-sectional view of externally integrated connector taken along line 3C showing housing 23 and at least one connecting wire 30 in greater detail. Externally integrated connector 22 is configured such that a sensor 34 may be coupled to connector 22 in housing 23 so that data is transferred from the patient through connecting wire 30. Similarly, FIG. 3D shows a side cross-sectional view of an internally integrated connector 22 along cable 20 and FIG. 3E shows a side view of an internally integrated connector along cable 20. By integrating connector 22 internally as part of cable 20, there is less of a chance of any interference with other parts of cable 20 or other materials used to monitor a patient. Further, by eliminating individual lead wires, the present invention reduces the chances of cable 20 becoming tangled on itself. In addition, a care giver need not inspect and replace individual lead wires. In applying cable 20 to a patient, a care giver does not need to look at cable 20. Instead, the care giver may simply slide cable 20 along between his or her fingers to apply each sensor in turn when feeling the appropriate connector 22 or housing 23 along the length of cable 20.

According to an exemplary embodiment of the present invention, cable 20 may include bumps or swells at the location of each connector 22 (e.g., for cables with internally integrated connectors) in order to assist a care giver in locating the proper connector and/or sensor position along cable 20. For example, as shown in FIGS. 3D and 3E, cable 20 includes a slight swell or raise at each connector 22. Alternatively, cable 20 may have other types of indicators that allow a care giver to locate the proper connector and/or sensor. For example, cable 20 may include dips, indentations, notches, etc. Further, cable 20 may also include connectors 22 that are completely integrated in cable 20. For example, FIG. 1B shows a connector 22 that is entirely integrated within cable 20. Sensor 34 may then be coupled to cable 20 by way of housing 23.

Figure 4:
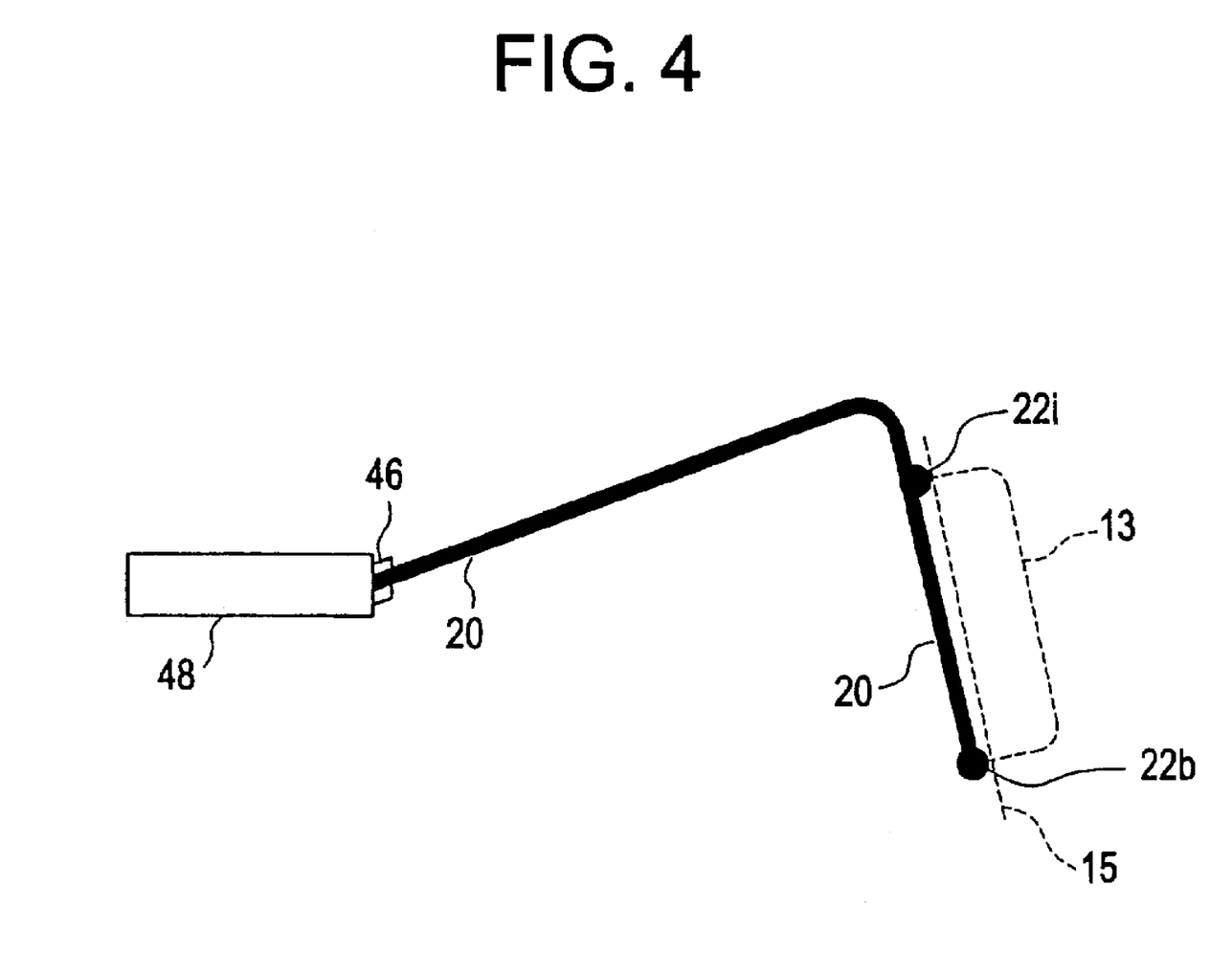
FIG. 4 is a partial view of a monitoring cable showing sensors in an in-line configuration as attached to a patient according to an exemplary embodiment.

The design of the exemplary embodiment in FIG. 4 helps minimize noise distortion between sensors. Each of the connectors 22, as shown by connectors 22b and 22i, lie in an in-line sequence with respect to one another. Therefore, instead of each connecting wire hanging freely at a different length along cable 20, the connectors attach to the connecting wires 30 housed within cable 20 at specified locations. This allows each of connecting wires 30 to extend the entire length of cable 20 from the first end 26 to the second end 28. This type of configuration is advantageous because it provides a common path for interference signals which can be identified and then eliminated by a difference amplifier.

Figure 5:
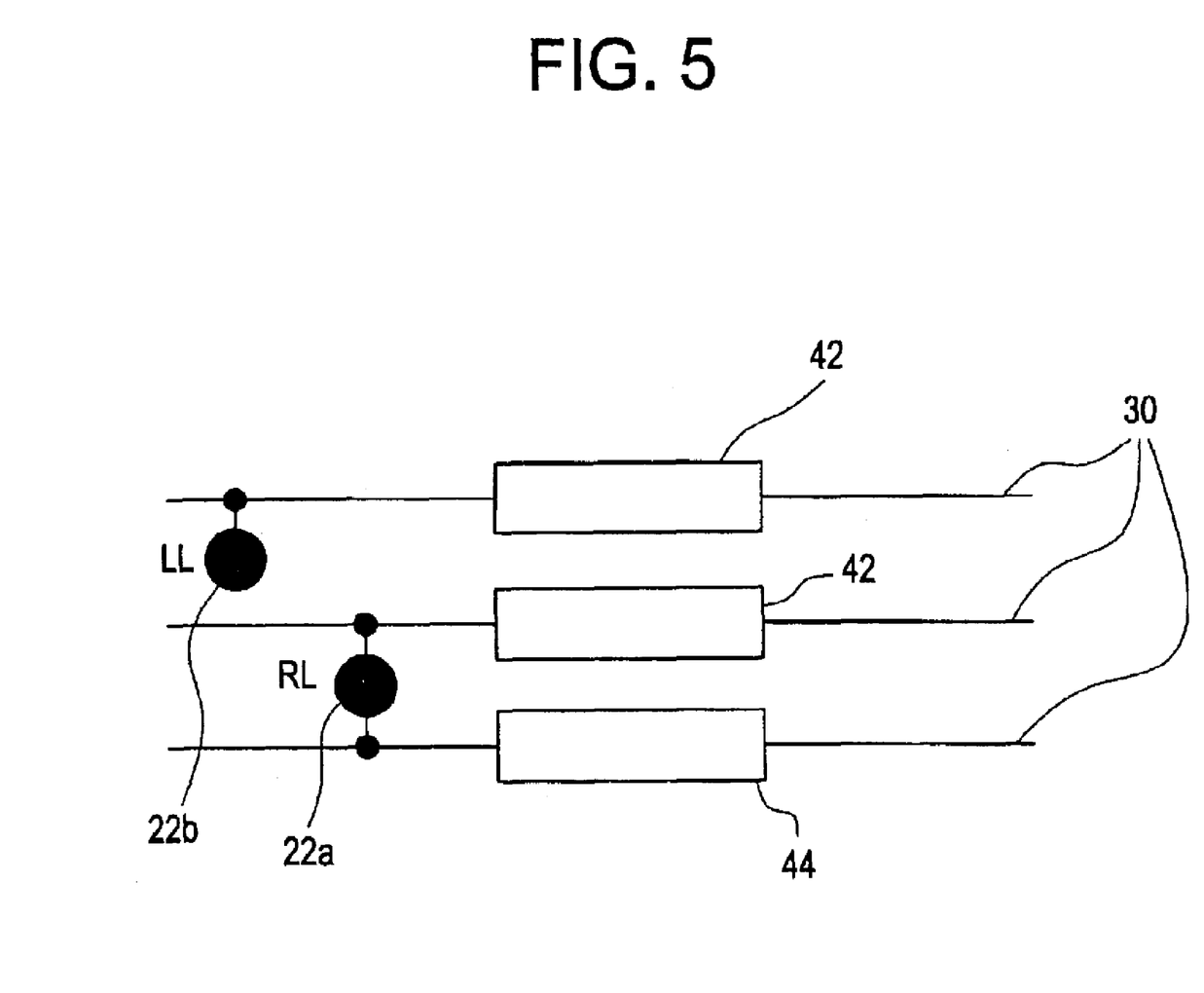
FIG. 5 is a schematic diagram of defibrillation resistors and an identity resistor located in a monitoring cable according to an exemplary embodiment.

Referring to FIG. 5, cable 20 may be provided with defibrillation resistors 42. Resistors 42 may be present for each sensor. Additionally, cable 20 may include a cable identity resistor 44 for the first sensor attached at connector 22a. Consequently, the right leg electrode located at connector 22a, in effect, attaches functionally to two wires 30. Further, other sensors coupled to cable 20 may be attached to multiple wires 30. For instance, non-ECG connectors 24 may require more than one connecting wire 30 to obtain accurate data from a patient. Thus, non-ECG sensors could effectively attach to more than one wire 30 in certain circumstances.

Cable 20 may also include a mating connector 46 located at first end 26 of cable 20. Mating connector 46 may include a number of contact portions each connected to a respective one of the connecting wires 30 to couple cable 20 to monitoring equipment, shown as but not limited to instrument 48. Further, cable 20 may be manufactured to fit different sized individuals. For example, according to a preferred embodiment, three different sized cables 20 are included in a patient monitoring system in order to fit small, medium and large individuals as necessary. In addition, cable 20 may be durable and flexible to accommodate different patient monitoring needs.

Figure 6:
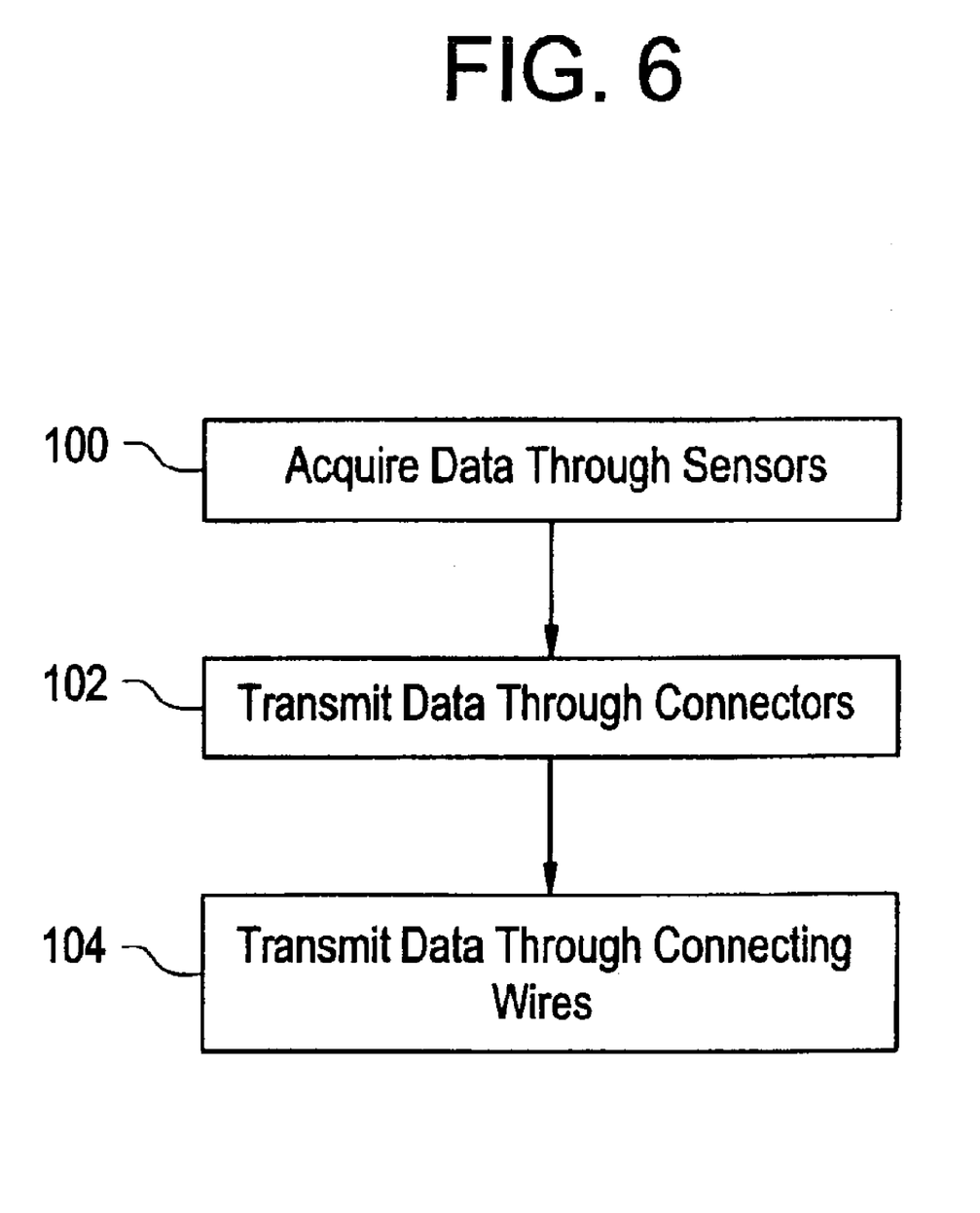
FIG. 6 is a flow diagram according to an embodiment of the present invention.

FIG. 6 is a flow diagram according to one embodiment of the present invention. Data is acquired through a plurality of sensors arranged in an in-line sequence from a first end to a second end of a monitoring cable at operation 100. The plurality of sensors may include: (a) a right leg electrode positioned as a first sensor in the in-line sequence; (b) a left hipbone electrode positioned as a second sensor in the in-line sequence; (c) at least one midsection electrode positioned after the second sensor in the in-line sequence; (d) a right side superior electrode positioned after the at least one midsection electrode in the in-line sequence; and (e) a left side superior electrode positioned after the right side superior electrode in the in-line sequence. Data is transmitted through a plurality of connectors coupled with the plurality of sensors at operation 102. In addition, data is transmitted from the plurality of connectors through a plurality of connecting wires that are housed within an outer cable and extend from a first end to a second end of the outer cable at operation 104.

While the embodiments and application of the invention illustrated in the figures and described above are presently preferred, it should be understood that these embodiments are offered by way of example only. Accordingly, the present invention is not limited to a particular embodiment, but extends to various modifications that nevertheless fall within the scope of this application.

What is claimed is:

1. A monitoring cable for use with a patient monitoring system, the monitoring cable comprising:
   a first end and a second end;
   an outer sheathing extending from the first end to the second end;
   a plurality of connecting wires, the plurality of connecting wires each being housed within the outer sheathing, wherein the outer sheathing provides insulation for each of the plurality of connecting wires, and further electrically insulates each of the plurality of connecting wires from each other;
   a plurality of connectors being arranged along the monitoring cable to correspond with a desired location on the patient, the plurality of connectors each being coupled to at least one of the plurality of connecting wires;
   a cable identity resistor coupled to a first one of the plurality of connecting wires; and
   a first sensor coupled to a first one of the plurality of connectors, wherein the first one of the plurality of connectors is coupled to the cable identity resistor and further coupled to a second one of the plurality of connecting wires, such that the first sensor is coupled to the first and second one of the plurality of connecting wires,
   wherein at least one of the plurality of connectors is arranged to only couple with an ECG sensor;
   wherein at least one of the plurality of connectors is arranged to only couple with a non-ECG sensor.

2. The monitoring cable of claim 1, wherein the plurality of connecting wires each extend from the first end to the second end of the monitoring cable, the plurality of connectors being located there between.

3. The monitoring cable of claim 2, further comprising a plurality of sensors arranged in an in-line sequence from the first end to the second end of the monitoring cable, the plurality of sensors including a right leg electrode positioned as the first sensor in the in-line sequence.

4. The monitoring cable of claim 1, wherein the plurality of sensors include at least one of the following: (a) a respiration sensor; (b) a non-invasive blood pressure sensor; (c) a pulse oxygen sensor; (d) body position or activity sensor; (e) a skin galvonic response sensor; and (f) a skin temperature sensor.

5. The monitoring cable of claim 1, wherein the plurality of sensors include the following: (a) a respiration sensor; (b) a non-invasive blood pressure sensor; (c) a pulse oxygen sensor.

6. The monitoring cable of claim 5, wherein the plurality of sensors further include the following: (d) a body position or activity sensor; (e) a skin galvonic response sensor; and (f) a skin temperature sensor.

7. The monitoring cable of claim 1, wherein at least one of the plurality of connectors is internally integrated as part of the monitoring cable.

8. The monitoring cable of claim 1, wherein at least one of the plurality of connectors is externally integrated as part of the monitoring cable and has a generally obtuse shape.

9. The monitoring cable of claim 1, wherein the monitoring cable further comprises defibrillation protection resistors for each of a plurality of sensors.

10. The monitoring cable of claim 1, wherein the monitoring cable is substantially circular in cross-section.

11. The monitoring cable of claim 1, further comprising an interface located at the first end of the monitoring cable, the interface including a plurality of contact portions each connected to a respective one of the plurality of connecting wires to couple the monitoring cable to monitoring equipment.

12. A monitoring cable for use with a patient monitoring system, the monitoring cable comprising:
   a plurality of connecting wires housed within an outer covering of the monitoring cable, the plurality of connecting wires each extending from a first end to a second end of the monitoring cable, wherein the outer covering provides insulation for each of the plurality of connecting wires, and further electrically insulates each of the plurality of connecting wires from each other;
   a plurality of sensors arranged in an in-line sequence between the first end and the second end of the monitoring cable, each sensor being coupled to at least one connecting wire, the plurality of sensors including a right leg electrode positioned as a first sensor in the in-line sequence and at least one non-ECG sensor;
   a cable identity resistor coupled to the first one of the plurality of connecting wires; and
   a first sensor coupled to a first one of the plurality of connectors, wherein the first one of the plurality of connectors is coupled to the cable identity resistor and further coupled to a second one of the plurality of connecting wires, such that the first sensor is coupled to the first and second one of the plurality of connecting wires,
   wherein the plurality of sensors are coupled to the plurality of connecting wires by way of a plurality of connectors;
   wherein at least one of the plurality of connectors is arranged to only couple with an ECG sensor;
   wherein at least one of the plurality of connectors is arranged to only couple with a non-ECO sensor.

13. The monitoring cable of claim 12, wherein the plurality of sensors further comprise a respiration sensor, a non-invasive blood pressure sensor, and a pulse oxygen sensor.

14. The monitoring cable of claim 12, wherein at least one of the plurality of connectors is internally integrated as part of the monitoring cable.

15. The monitoring cable of claim 14, wherein at least one of the plurality of connectors is externally integrated as part of the monitoring cable and has a generally obtuse shape.

16. A patient monitoring system comprising:
   a plurality of connecting wires, the plurality of connecting wires being housed within an outer sheathing of at least one monitoring cable, the plurality of connecting wires each extending from a first end to a second end of the at least one monitoring cable, wherein the outer sheathing provides insulation for each of the plurality of connecting wires, and further electrically insulates each of the plurality of connecting wires from each other;
   an interface located at the first end of the at least one monitoring cable, the interface including a plurality of contact portions each connected to a respective one of the plurality of connecting wires;
   a plurality of connectors each coupled to at least one of the plurality of connecting wires;
   monitoring equipment coupled to the interface located at the first end of the monitoring cable;
   a cable identity resistor coupled to a first one of the plurality of connecting wires; and
   a first sensor coupled to a first one of the plurality of connectors, wherein the first one of the plurality of connectors is coupled to the cable identity resistor and further coupled to a second one of the plurality of connecting wires, such that the first sensor is coupled to the first and second one of the plurality connecting wires,
   wherein at least one of the plurality of connectors is an ECG connector that is arranged to only couple with an ECG sensor; and
   wherein at least one of the plurality of connectors is a non-ECG connector that is arranged to only couple with a non-ECG sensor.

17. The patient monitoring system of claim 16, wherein the plurality of connectors are integrally formed in the at least one monitoring cable to create a substantially smooth cable surface.

18. The patient monitoring system of claim 17, wherein at least one of the plurality of connectors is internally integrated as part of the at least one monitoring cable.

19. The patient monitoring system of claim 17, wherein at least one of the plurality of connectors is externally integrated as part of the at least one monitoring cable.

20. The patient monitoring system of claim 16, further comprising a plurality of sensors coupled to the plurality of connecting wires by way of the plurality of connectors.

21. The patient monitoring system of claim 20, wherein the sensors further comprise a plurality of ECG sensors.

22. The patient monitoring system of claim 20, wherein the plurality of sensors further comprise at least one non-ECG sensor.

23. The patient monitoring system of claim 22, wherein the plurality of sensors include at least one of the following: (a) a respiration sensor; (b) a non-invasive blood pressure sensor; (c) a pulse oxygen sensor; (d) a body position or activity sensor; (e) a skin galvonic response sensor; and (f) a skin temperature sensor.

24. The patient monitoring system of claim 22, wherein the plurality of sensors include the following: (a) a respiration sensor; (b) a non-invasive blood pressure sensor; (c) a pulse oxygen sensor; (d) a skin galvonic response sensor; and (e) a skin temperature sensor.

25. The patient monitoring system of claim 22, wherein the plurality of sensors include the following: (a) a respiration sensor; (b) a non-invasive blood pressure sensor; and (c) a pulse oxygen sensor.

26. The patient monitoring system of claim 16, wherein the patient monitoring system comprises a plurality of monitoring cables capable of fitting different sized individuals.

* * * * *